United States Patent [19]
Maeke et al.

[11] Patent Number: 4,734,506

[45] Date of Patent: Mar. 29, 1988

[54] 4-AMINO-3-IMIDAZOLIN-2-ONE

[75] Inventors: Siegfried Maeke, Raubling-Kirchdorf; Adolf Bauer; Hubert Vogt, both of Raubling; Helmut Wolf, Neubeuern, all of Fed. Rep. of Germany

[73] Assignee: Diamalt Aktiengesellschaft, Munich, Fed. Rep. of Germany

[21] Appl. No.: 911,268

[22] Filed: Aug. 4, 1986

Related U.S. Application Data

[62] Division of Ser. No. 581,852, Feb. 21, 1984, Pat. No. 4,623,730.

[30] Foreign Application Priority Data

Feb. 19, 1983 [DE] Fed. Rep. of Germany ....... 3305778

[51] Int. Cl.$^4$ ............................................. C07D 233/88
[52] U.S. Cl. .................................................. 548/308
[58] Field of Search ......................................... 548/308

[56] References Cited

FOREIGN PATENT DOCUMENTS 966395 10/1950 France ............................... 548/308

Primary Examiner—Henry R. Jiles
Assistant Examiner—Kurt G. Briscoe
Attorney, Agent, or Firm—Millen & White

[57] ABSTRACT

4-Amino-3-imidazolin-2-one and (2-methoxy-2-iminoethyl) urea are valuable intermediates for the production of pharmacologically active compounds.

1 Claim, 2 Drawing Figures

4-AMINO-3-IMIDAZOLIN-2-ONE

This is a division of application Ser. No. 581,852 filed Feb. 21, 1984, now U.S. Pat. No. 4,623,730.

BACKGROUND OF THE INVENTION

The present invention relates to two new compounds, 4-amino-3-imidazolin-2-one (=4-iminoimidazolidin-2-one) and (2-methoxy-2-iminoethyl)urea, methods for their preparation and their use, e.g., to prepare orotic acid.

Various methods for preparing orotic acid are known, e.g., as disclosed in German Pat. No. 2,502,951. However, these suffer from disadvantages, e.g., difficulty of purification of the desired product.

SUMMARY OF THE INVENTION

Accordingly, it is an object of this invention to provide new, useful compounds and methods for their preparation.

It is another object of this invention to provide such compounds useful for preparation of orotic acid in pure form.

Upon further study of the specification and appended claims, further objects and advantages of this invention will become apparent to those skilled in the art.

These objects have been achieved by providing 4-amino-3-imidazolin-2-one and (2-methoxy-2-iminoethyl)urea, urea, as well as a process for the preparation of 4-amino-3-imidazolin-2-one and (2-methoxy-2-iminoethyl)urea, comprising reacting cyanomethylurea in an alcohol containing 1–4 carbon atoms in the presence of catalytic amounts of a base, especially using, per mole of cyanomethylurea, 0.001–0.2 mole of sodium hydroxide or potassium hydroxide, most especially by conducting the reaction at a temperature of 0°–100° C.

These objects have also been attained by using 4-amino-3-imidazolin-2-one and (2-methoxy-2-iminoethyl)urea for the production of orotic acid, e.g., by reacting these compounds in the presence of basic catalysts with glyoxylic acid. (2-methoxy-2-iminoethyl)urea can also be used for the preparation of 4-amino-3-imidazolin-2-one.

BRIEF DESCRIPTION OF THE DRAWINGS

Various other objects, features and attendant advantages of the present invention will be more fully appreciated as the same becomes better understood when considered in conjunction with the accompanying drawings, and wherein.

Figure 1:
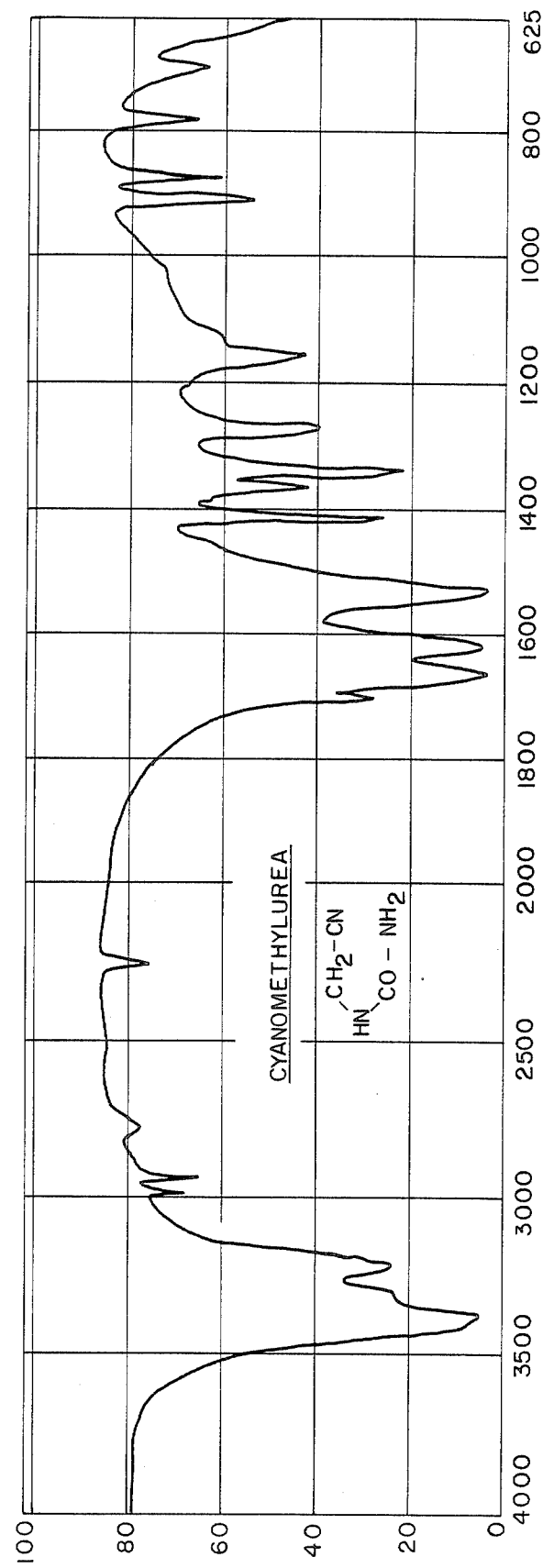
FIG. 1 shows the IR spectrum of cyanomethylurea.

DETAILED DISCUSSION 4-amino-3-imidazolin-2-one and (2-methoxy-2-iminoethyl)urea can be obtained by reacting cyanomethylurea in an alcohol containing 1–4 carbon atoms in the presence of catalytic amounts of a base. Suitable alcohols in which the process of this invention can be performed include, for example, $C_{1-4}$-alkanols, e.g., methanol, ethanol, isopropanol, a butanol, etc. The reaction is preferably conducted by reacting 50–1,500 g and especially 250–1,500 g of cyanomethylurea per liter of alcohol. Suitable catalytic bases include, for example: quaternary ammonium bases, e.g., tetramethylammonium hydroxide or choline, alkali metal alcoholates, e.g., $C_{1-4}$-alkanoates, e.g., sodium or potassium alcoholate derived from the alcohol used as the solvent; or alkali metal or alkaline earth metal hydroxides, e.g., sodium hydroxide, potassium hydroxide, calcium hydroxide, etc., and others. Typically, 0.001–0.2 mole of catalyst is used per mole of starting material, e.g., cyanomethylurea. In general, reaction compatible bases will be useful if they are strong bases, e.g., having PKb's greater than 5 or if they achieve a pH in the reaction solution of greater than 9 when used in appropriate amounts. The usual reaction period is about 0.2–30 hours at room temperature and is conventionally correspondingly shortened by performing the reaction at an elevated temperature. Generally, the temperature is 0°–100° C.

The foregoing general conditions apply to the process irrespective of which new compound is being prepared unless otherwise indicated in the following which discusses the variations used to preselect which compound is prepared. If the reaction is conducted in methanol at temperatures of 10°–35° C., (2-methoxy-2-iminoethyl)urea is obtained within 0.2–20 hours. If the reaction is effected at an elevated temperature, e.g., >35°–100° C. in any alcohol, or if an alcohol other than methanol is used, then 4-amino-3-imidazolin-2-one is produced. When the reaction is conducted in methanol at temperatures near the 35° C. point, e.g., 35°–50° C., a mixture of both products of the invention will usually be obtained. When this occurs, the products can be separated conventionally, e.g., by recrystallization or chromatographically. At the higher temperatures, e.g., above about 50° C., and especially under reflux, essentially only 4-amino-3-imidazolin-2-one is produced. At the lower temperatures in methanol, especially less than 35° C., essentially only (2-methoxy-2-iminoethyl)urea is produced.

It was surprising to a person skilled in the art that, under the process conditions of this invention, high yields of 4-amino-3-imidazolin-2-one and/or of (2-methoxy-2-iminoethyl)urea would be formed. One skilled in the art could not expect that cyanomethylurea would react under such gentle conditions. Furthermore, a person skilled in the art could not foresee that (2-methoxy-2-iminoethyl)urea would exhibit such low solubility in methanol, and that 4-amino-3-imidazolin-2-one would be so sparingly soluble in the remaining alcohols that the reaction equilibria are shifted in favor of formation of these products. This basic reaction can also be conducted when the ethyl-substituted N-atom has a $C_{1-4}$-alkyl group substituted in place of its remaining H-atom and/or when the other N-atom of the urea portion of the molecule has one or two $C_{1-4}$-substituents (the latter option being applicable only in the reaction which prepares (2-methoxy-2-iminoethyl)urea).

Because of their active methylene groups, 4-amino-3-imidazolin-2-one and (2-methoxy-2-iminoethyl)urea are excellently suitable as components for aldol condensation reactions. Accordingly, they are valuable intermediates for synthesis of commercially exploitable compounds. It is possible, for example, to use 4-amino-3-imidazolin-2-one and/or (2-methoxy-2-iminoethyl)urea for the manufacture of orotic acid, a compound useful as a vitamin, a feed supplement and a uricosuric (U.S. Pat. No. 3,086,917).

The production of orotic acid as described above using 4-amino-3-imidazolin-2-one and (2-methoxy-2-iminoethyl)urea can be accomplished using the isolated compounds proper and also using reaction mixtures containing these compounds. Preferably the orotic acid synthesis is effected in an aqueous or aqueous-alcoholic phase, wherein the alcohols typically are $C_{1-4}$-alkanols, utilizing about 0.1–5 moles of 4-amino-3-imidazolin-2-one or (2-methoxy-2-iminoethyl)urea per liter of solvent. Per mole of 4-amino-3-imidazolin-2-one or of (2-methoxy-2-iminoethyl)urea, 0.5–2.0 moles of glyoxylic acid is utilized, preferably 0.8–1.2 moles of this compound. The reaction can be conducted using the above-mentioned basic (alkaline) catalysts. Preferably, sodium hydroxide or potassium hydroxide is employed in an amount that a basicity of 0.1–5N prevails at the end of the reaction. The reaction temperature is preferably 20°–100° C. and the reaction time is generally 0.5–10 hours. At the end of the reaction, the mixture is either neutralized, thus obtaining the sodium potassium, etc. salt of orotic acid, or strongly acidified, thus producing the orotic acid monohydrate.

As compared with the process known from German Pat. No. 2,502,951, the mode of operation of this invention for producing orotic acid is distinguished, inter alia, by a superior purity of the product produced. This is of special significance, since orotic acid can be purified only with difficulty by recrystallization.

The conversion of (2-methoxy-2-iminoethyl)urea to 4-amino-3-imidazolin-2-one is carried out under the same conditions as the reaction used to prepare 4-amino-3-imidazolin-2-one from cyanomethylurea.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A suspension of 198 g of cyanomethylurea in 300 ml of ethanol is heated under reflux, combined with 6 ml of 8N sodium hydroxide solution (or with 7 ml of 7N potassium hydroxide solution), and heated for another 5 minutes after fading of the exothermic reaction. The reaction mixture is then allowed to cool, the thus-separated product is filtered off, washed with a small amount of ice-cooled ethanol, dried, and the product is 194 g of 4-amino-3-imidazolin-2-one (=98% of theory).

Practically the same yields are obtained by utilizing methanol or isopropanol in place of ethanol.

EXAMPLE 2

100 g of cyanomethylurea is combined with a mixture of 300 ml of methanol and 5 ml of 8N sodium hydroxide solution and stirred for 3 hours at 25°30° C. The mixture is allowed to cool to 20° C., the resultant product is removed by filtration, washed with a small amount of ice-cold methanol, and dried under vacuum, thus obtaining 92.6 g of (2-methoxy-2-iminoethyl)urea (=70% of theory).

EXAMPLE 3

26 g of (2-methoxy-2-iminoethyl)urea is combined with a mixture of 50 ml of ethanol and 1 ml of 8N sodium hydroxide solution and heated under reflux for 30 minutes. The reaction mixture is worked up as described in Example 1, thus producing 18.6 g of 4-amino-3-imidazolin-2-one (=94.7% of theory).

| Characterization of Compounds of This Invention was Compared with Cyanomethylurea | | | | | |
|---|---|---|---|---|---|
| | MP °C. | N Calc. (%) | N Found (%) | Solubility in 100 ml $H_2O$ at Room Temp. (g) | λ max |
| Cyanomethylurea $C_3H_5N_3O$; 99.09 | 140–142 | 42.40 | 42.32 | 4.3 | 198 nm |
| 4-Amino-3-imidazolin-2-one $C_3H_5N_3O$; 99.09 | — (D > 350° C.) | 42.40 | 42.35 | 0.4 | 230 nm |
| (2-Methoxy-2-iminoethyl)urea $C_4H_9N_3O_2$; 131.14 | 108–110 (D) | 32.04 | 31.97 | 9.8 | 198 nm |

Figure 2:
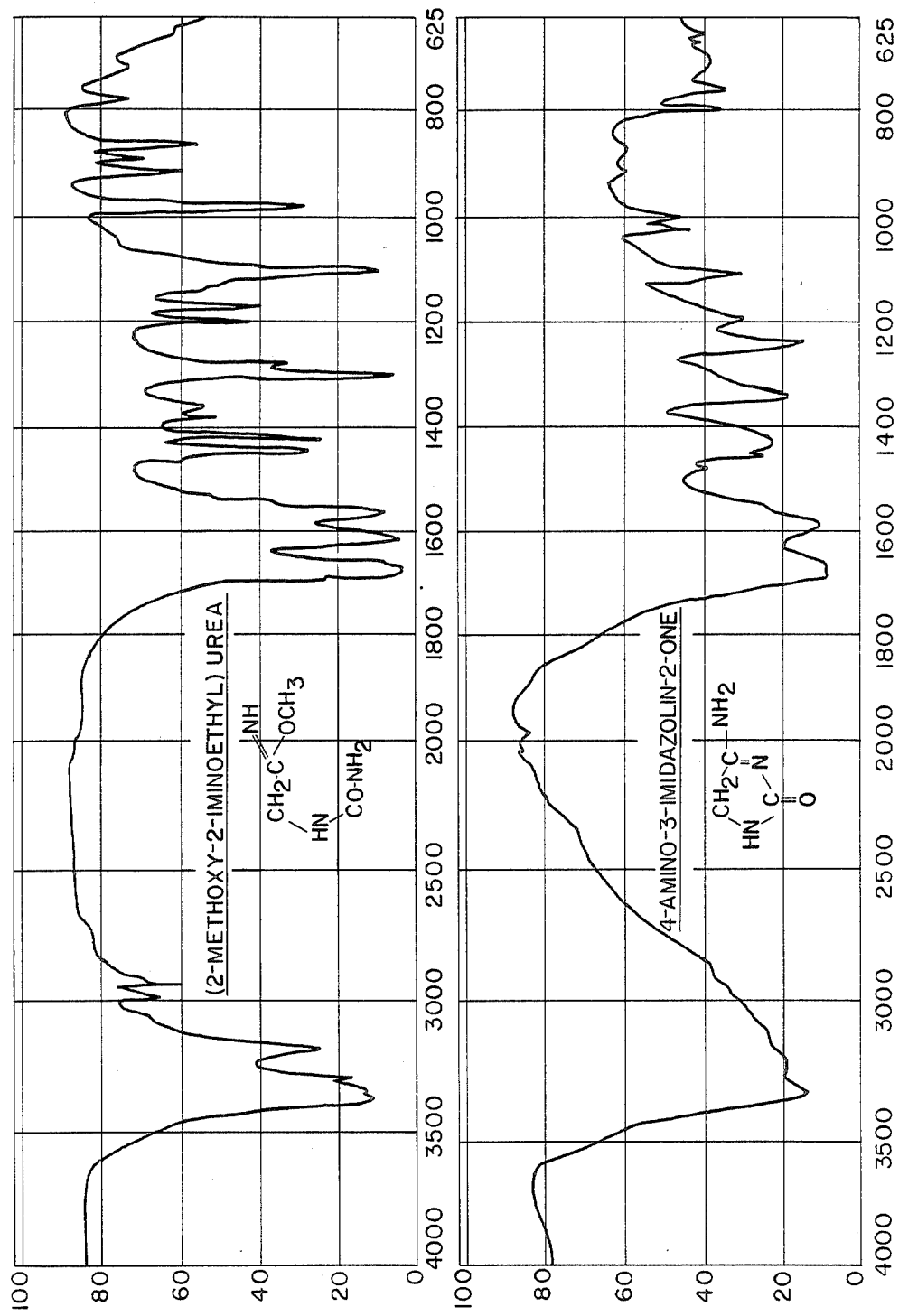
FIG. 2 shows the IR spectrum of (2-methoxy-2-iminoethyl)urea and 4-amino-3-imidazolin-2-one.

For further characterization, see IR spectra in FIGS. 1 and 2.
[D = Decomposition]

EXAMPLE 4

At 60° C., 62.5 ml of 8N sodium hydroxide solution is added dropwise within one hour to 5 g of amino-2-imidazolin-2-one and 4.6 g of glyoxylic acid in 200 ml of water, and the mixture is further stirred for 2 hours at this temperature. Subsequently the pH is set to 6 with concentrated hydrochloric acid, thus precipitating sodium orotate. After vacuum-filtering, washing, and drying, 6.9 g of this salt is obtained=78% of theory.

By adding as an alternative, after termination of the reaction, an excess of hydrochloric acid up to pH 1, then orotic acid monohydrate is precipitated. After isolation and drying at a moderate temperature, 6.8 g of the monohydrate is obtained, corresponding to 78% of theory.

The identity of the compounds is confirmed by IR spectra.

EXAMPLE 5

A suspension of 57 g of cyanomethylurea in 45 ml of methanol is heated to boiling under agitation, combined with 3 ml of 8N sodium hydroxide solution, and heated under reflux for 30 minutes. The reaction mixture is then allowed to cool down to 30° C., 550 ml of water and 90 g of 50% strength glyoxylic acid are added thereto, and the mixture is neutralized with 8N sodium hydroxide solution at a temperature of maximally 30° C. until a pH of 6.5 has been attained. The mixture is then heated to 55°–60° C., 225 ml of 8N sodium hydroxide solution is added dropwise thereto at this temperature within one hour, and the mixture is stirred for another 2 hours. Then about 150 ml of aqueous methanol is removed by distillation to 95° C.; the mixture is heated for one hour under reflux and gently acidified with concentrated nitric acid. The mixture is allowed to cool down to room temperature, the thus-separated crystallized product is filtered off, washed with water, and dried under vacuum, thus obtaining 72 g of orotic acid (=71.8% of theory).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. 4-amino-3-imidazolin-2-one.

* * * * *